(12) United States Patent
Kashiwagi (10) Patent No.: US 8,140,355 B2
(45) Date of Patent: Mar. 20, 2012

(54) HEALTH MANAGEMENT SYSTEM, PERSONALIZING TERMINAL AND HEALTH MANAGEMENT DATA INTEGRATING METHOD

(75) Inventor: Koichi Kashiwagi, Ichikawa (JP)

(73) Assignee: Sharp Kabushiki Kaisha, Osaka (JP)

( * ) Notice: Subject to any disclaimer, the term of this patent is extended or adjusted under 35 U.S.C. 154(b) by 209 days.

(21) Appl. No.: 12/307,610

(22) PCT Filed: Jul. 2, 2007

(86) PCT No.: PCT/JP2007/063231
§ 371 (c)(1),
(2), (4) Date: Jun. 3, 2009

(87) PCT Pub. No.: WO2008/004518
PCT Pub. Date: Jan. 10, 2008

(65) Prior Publication Data
US 2010/0088109 A1 Apr. 8, 2010

(30) Foreign Application Priority Data

Jul. 7, 2006 (JP) ................................. 2006-188152

(51) Int. Cl.
*G06Q 10/00* (2006.01)
*G06Q 50/00* (2006.01)
(52) U.S. Cl. .............................................. 705/2; 705/3
(58) Field of Classification Search .................... 705/2–3
See application file for complete search history.

(56) References Cited

U.S. PATENT DOCUMENTS

2005/0101844 A1* 5/2005 Duckert et al. ............... 600/300
2008/0162185 A1* 7/2008 Klabunde et al. ................. 705/2

FOREIGN PATENT DOCUMENTS

| JP | 10-326245 | 12/1998 |
| JP | 10-326245 A | 12/1998 |
| JP | 2001-321344 | 11/2001 |
| JP | 2002-056099 | 2/2002 |
| JP | 2002-329008 | 11/2002 |

(Continued)

OTHER PUBLICATIONS

International Search Report for PCT/JP2007/063231 mailed Sep. 11, 2007.

(Continued)

*Primary Examiner* — Luke Gilligan
*Assistant Examiner* — Joseph Burgess
(74) *Attorney, Agent, or Firm* — Nixon & Vanderhye P.C.

(57) ABSTRACT

To provide a health management system including health data measuring devices shared by a plurality of persons and health data measuring devices used by an individual together, which unites health data measured by each health data measuring device with the user practicing the measurement to allot user ID etc. to the health data as well as to provide a personalizing terminal and a health management data integrating method. A personalizing terminal 160 receives attribute information and health data from common devices 110 to 130 as the health data measuring devices shared by the plurality of persons, gives a user ID to the health data at a user ID allocator 163 and transmits the health data and the aforementioned attribute information to a gateway 170. Gateway apparatus 170 integrates the attribute information and health data received from personalizing terminal 160, personal device 140 or 150 and transmits the data to a server apparatus 310 in a data center 300.

6 Claims, 6 Drawing Sheets

FOREIGN PATENT DOCUMENTS

| | | |
|---|---|---|
| JP | 2002-329008 A | 11/2002 |
| JP | 2003-210420 | 7/2003 |
| JP | 2004-201987 | 7/2004 |
| JP | 2004-283570 | 10/2004 |
| JP | 2004-283570 A | 10/2004 |
| JP | 2005-39782 A | 2/2005 |
| WO | WO0028460 | 5/2000 |

OTHER PUBLICATIONS

English translation of the International Preliminary Report on Patentability mailed Jan. 29, 2009 in corresponding PCT Application No. PCT/ JP2007/063231.

European Search Report for corresponding EP Application No. 07768006.4 dated Dec. 20, 2011.

* cited by examiner

| Number of attributes | Device ID | Maker name | Model No. | Serial No. | ... |
|---|---|---|---|---|---|

FIG. 8

| Device ID | Number of data items | Item ID1 | Number of attributes | Title 1 | Unit 1 | Scale 1 | ... | Item ID2 | Number of attributes | Title 2 | Unit 2 | Scale 2 | ... | ... |

⎵_________ Health data item 1 _________⎵  ⎵_________ Health data item 2 _________⎵

FIG. 9

| Device ID | Number of data | Data ID1 | Data 1 | Data ID1 | Data 2 | Data ID2 | Data 3 | ... |

⎵___ Data 1 ___⎵ ⎵___ Data 2 ___⎵ ⎵___ Data 3 ___⎵

| User ID | Device ID | Number of data | Data ID1 | Data 1 | Data ID1 | Data 2 | Data ID2 | Data 3 | ... |

⎵___ Data 1 ___⎵ ⎵___ Data 2 ___⎵ ⎵___ Data 3 ___⎵

| Device ID | Maker name | Model No. | Serial No. | ... |
|---|---|---|---|---|
| ⋮ | ⋮ | ⋮ | ⋮ | ⋮ |

HEALTH MANAGEMENT SYSTEM, PERSONALIZING TERMINAL AND HEALTH MANAGEMENT DATA INTEGRATING METHOD

This application is the U.S. national phase of International Application No. PCT/JP2007063231 filed 2 Jul. 2007 which designated the U.S. and claims priority to Japanese Patent Application No. 2006-188152 filed 7 Jul. 2006, the entire contents of each of which are hereby incorporated by reference.

TECHNICAL FIELD

The present invention relates to a health management system for integrating and managing a variety of data associated with the health of a user by using networks, as well as relating to a personalizing terminal and an integrating method of health management data in the health management system.

BACKGROUND ART

Recently, in the home health care- and self-care-related industries, health management systems for managing and integrating the health management data (which will be referred to hereinbelow as "health data") measured by various kinds of health data measuring devices in an in-home PC (Personal Computer) or in a data center on the internet, by making use of network technologies, have been developed and services using this have started to appear.

A technology of integrating and managing health data of a user, measured by health data measuring devices such as a weighing machine, blood pressure gage and pedometer, for example, in a PC and allowing the user to check his/her own health data on the PC so as to maintain and promote his/her health, has been disclosed (e.g., see patent document 1).

Also, there has been a disclosure of a technology of transmitting data that was measured by a health data measuring device to a data center on the internet by way of a cellular phone (e.g., see patent document 2).

In the system of patent document 2, a health data measuring device and a cellular phone are connected by way of a data transmitter. The data transmitter, when it receives new health data from the health data measuring device, generates access information for transmitting the new health data to a data center and transfers the information to the cellular phone. The cellular phone makes access to the data center in accordance with the access information and transmits the health data.
Patent document 1:
Japanese Patent Application Laid-open 2004-283570
Patent document 2:
Japanese Patent Application Laid-open 2005-039782

DISCLOSURE OF INVENTION

Problems to be Solved by the Invention

By the way, there are various kinds of health data measuring devices for home health care and self-care. As one viewpoint for classifying these, personal or common use, explicitly, whether a device is a personal device for a particular individual or a common device for family members etc., can be mentioned.

The problem to be considered in this case is the way of determining the user (measuring person) when a common device is used, or the way of uniting measured data with its user.

In patent document 1, a pedometer is exemplified as an individual personal device and a weighing machine and a blood pressure gauge are exemplified as common devices. A personal device is tuned up so that personal information such as a user ID and the like is input, in advance, into the device, and the data, when it is transmitted to a PC, is transmitted with the user ID. In contrast to this, a common device is tuned up so that individuals are allotted to buttons provided for the device body (decided by the family) and the user is identified by pressing the button allotted for the user, and the data is transmitted with the user ID.

However, the number of buttons provided for a common device is limited. For example, when a device is used in a common space such as an old people's home or the like, or used by an unspecified large number of people, it is impossible to deal with. Though there are some countermeasures considered such as increasing the number of buttons, manipulation of the input method such as use of combination of buttons with few buttons, use of an input device instead of buttons and the like, these countermeasures entail with other problems such as device design, operativity and frequent entry errors.

Accordingly, use of user identification buttons in a common device for uniting health data with the user cannot bring about a drastic solution.

Further, in patent document 2, the health data measuring device is presumed to be used as an individual personal device, and there is no disclosure about the method of distinguishing the users and allocating IDs to health data in the common device.

The present invention is to provide a health management system including health data measuring devices shared by a plurality of persons and health data measuring devices used by an individual together, which unites the health data measured by each health data measuring device (health data measuring apparatus) with the user who practiced the measurement so as to allot user ID etc. to the health data as well as to provide a personalizing terminal and a health management data integrating method.

Means for Solving the Problems

In view of the above circumstances, the health management system of the first invention resides in a health management system including a health data measuring apparatus for measuring data relating to health of a user, a personalizing terminal for integrating the data and a gateway apparatus, characterized in that the health data measuring apparatus includes: a data measuring unit for measuring or calculating health management data; and a transmitter for transmitting the health management data to the personalizing terminal or the gateway apparatus, the personalizing terminal includes: a user information storage having user identification information stored therein; a user identification information allocator for allotting the user identification information extracted from the user information storage to health management data received from the health data measuring apparatus and having no user identification information; and, a transmitter for transmitting the health management data allotted with the user identification information to the gateway apparatus, and the gateway apparatus includes: a data transmitter for transmitting the health management data received from the health data measuring apparatus or the personalizing terminal to a server apparatus.

The health management system according to the second invention is characterized in that the measuring unit of the health data measuring apparatus or a receiver of the personalizing terminal stores device attribute information on the health data measuring apparatus and attribute information on the health management data into an associated device attribute and health data attribute storage, and the transmitter of the health data measuring apparatus or the transmitter of the personalizing terminal transmits the device attribute information on the health data measuring apparatus and the attribute information on the health management data to the personalizing terminal or the gateway apparatus before, or simultaneously with, transmission of the health management data.

The health management system according to the third invention is characterized in that a receiver of the personalizing terminal receives device attribute information on the health data measuring apparatus and attribute information on the health management data, and converts an identifier included in the attribute information on the health management data into an identifier unique to the personalizing terminal and stores the result into a personalizing terminal attribute information storage and also creates and stores a table that shows a correspondence between the identifiers before and after conversion; and, when receiving health management data from the health data measuring apparatus, the receiver converts an identifier included in the health management data with reference to the table and device attribute information on the personalizing terminal, which are stored in the personalizing terminal attribute information storage, and the result is stored into a health data storage, and, the transmitter of the personalizing terminal reads out the attribute information on health management data after conversion and device attribute information on the personalizing terminal from the personalizing terminal attribute information storage and transmits them to the gateway apparatus before or simultaneously with transmission of the health management data after conversion of the identifier.

The personalizing terminal according to the fourth invention resides in a personalizing terminal for integrating data relating to health of a user, comprising: a receiver for receiving measured or calculated health management data from a health data measuring apparatus; a user information storage having user identification information stored therein; a user identification information allocator for allotting the user identification information extracted from the user information storage to the health management data having no user identification information; and, a transmitter for transmitting the health management data allotted with the user identification information to a gateway apparatus.

The personalizing terminal according to the fifth invention is characterized in that the receiver stores device attribute information on the health data measuring apparatus and attribute information on the health management data received from the health data measuring apparatus, into a device attribute and health data attribute storage; and, the transmitter transmits the device attribute information on the health data measuring apparatus and the attribute information on the health management data to the gateway apparatus before, or simultaneously with, transmission of the health management data.

The personalizing terminal according to the sixth invention is characterized in that the receiver receives device attribute information on the health data measuring apparatus and attribute information on the health management data, and converts an identifier included in the attribute information on the health management data into an identifier unique to the personalizing terminal and stores the attribute information into a personalizing terminal attribute information storage and also creates and stores a table that shows a correspondence between the identifiers before and after conversion; and, when receiving health management data from the health data measuring apparatus, the receiver converts an identifier included in the health management data with reference to the table and device attribute information on the personalizing terminal, which are stored in the personalizing terminal attribute information storage, and stores the result into a health data storage, and, the transmitter reads out the attribute information on health management data after conversion and the device attribute information on the personalizing terminal from the personalizing terminal attribute information storage and transmits them to the gateway apparatus before, or simultaneously with, transmission of the health management data after conversion of the identifier.

The health management data integrating method according to the seventh invention resides in a health management data integrating method for measuring and integrating data relating to health of users, comprising the steps of: causing a health data measuring apparatus to execute the steps of: measuring or calculating health management data; and, transmitting the health management data to a personalizing terminal or a gateway apparatus, causing the personalizing terminal to execute the steps of: allocating user identification information extracted from a user information storage to the health management data received from the health data measuring apparatus and having no user identification information; and, transmitting the health management data to the gateway apparatus, and causing the gateway apparatus to execute the step of transmitting the health management data received from the health data measuring apparatus or the personalizing terminal to a server apparatus.

The health management data integrating method according to the eighth invention is characterized by causing a measuring unit of the health data measuring apparatus to execute the step of storing device attribute information on the health data measuring apparatus and attribute information on the health management data into a device attribute and health data attribute storage, and causing transmitter of the health data measuring apparatus to execute the step of transmitting the device attribute information on the health data measuring apparatus and the attribute information on the health management data to the personalizing terminal or the gateway apparatus before, or simultaneously with, transmission of the health management data.

The health management data integrating method according to the ninth invention is characterized by causing a receiver of the personalizing terminal to execute the step of storing the device attribute information on the health data measuring apparatus and the attribute information on the health management data into a device attribute and health data attribute storage; and causing a transmitter of the personalizing terminal to execute the step of transmitting the device attribute information on the health data measuring apparatus and the attribute information on the health management data to the gateway apparatus before, or simultaneously with, transmission of the health management data.

The health management data integrating method according to the tenth invention is characterized by causing a receiver of the personalizing terminal to execute the steps of: receiving the device attribute information on the health data measuring apparatus and the attribute information on the health management data, converting an identifier included in the attribute information on the health management data into an identifier unique to the personalizing terminal, and storing the attribute information into a personalizing terminal attribute information storage; creating a table that shows a correspondence between the identifiers before and after conversion and storing the table into the personalizing terminal attribute information storage; when receiving the health management data from the health data measuring apparatus, converting an identifier included in the health management data with reference to the table and device attribute information on the personalizing terminal, which are stored in the personalizing terminal attribute information storage, and storing the result into a health data storage, and, causing a transmitter of the personalizing terminal to execute the step of reading out the attribute information on health management data after conversion and the device attribute information on the personalizing terminal from the personalizing terminal attribute information storage and transmitting them to the gateway apparatus before, or simultaneously with, transmission of the health management data after conversion of the identifier.

Advantage of the Invention

According to the present invention, in the health management system including the health data measuring device shared by a plurality of persons and the health data measuring device used by an individual together, it is possible to achieve integration and management of health data by uniting the health data measured by each health data measuring device with the user who practiced the measurement and allotting user ID etc. (user identification information) to the health data.

Also, according to the present invention, it is possible to regard a personalizing terminal as a virtual single personal device, hence it is no longer necessary for the health data measuring devices and gateway apparatus to convert individual pieces of attribute information in conformity with other devices, and it is possible to simplify transmission and reception of data between devices of different specifications.

Further, even when the attribute information of each device is modified, if the modified attribute information is transmitted to the personalizing terminal, the attribute information as the whole system can be updated, whereby revision of attribute information can be simplified.

DESCRIPTION OF REFERENCE NUMERALS 1 health management system
100 in-home system
110, 120, 130 common device
111, 141 health data measuring unit
112, 144, 164 data/information transmitter
113, 145 health data temporary storage
114, 147 attribute information storage
140, 150 personal device
142, 162, 172 user information unit
143, 163 user ID allocator
146, 167, 176 user information storage
160 personalizing terminal
161, 171 data/information receiver
165, 174 health data storage
166, 175 device attribute and health data attribute storage
168 personalizing terminal attribute information storage
170 gateway apparatus
173 server access and data transmitter
200 public line
300 data center
310 server apparatus

BEST MODE FOR CARRYING OUT THE INVENTION

The First Embodiment

Next, the embodiments of the health management system according to the present invention will be described with the illustrated examples.

Figure 1:
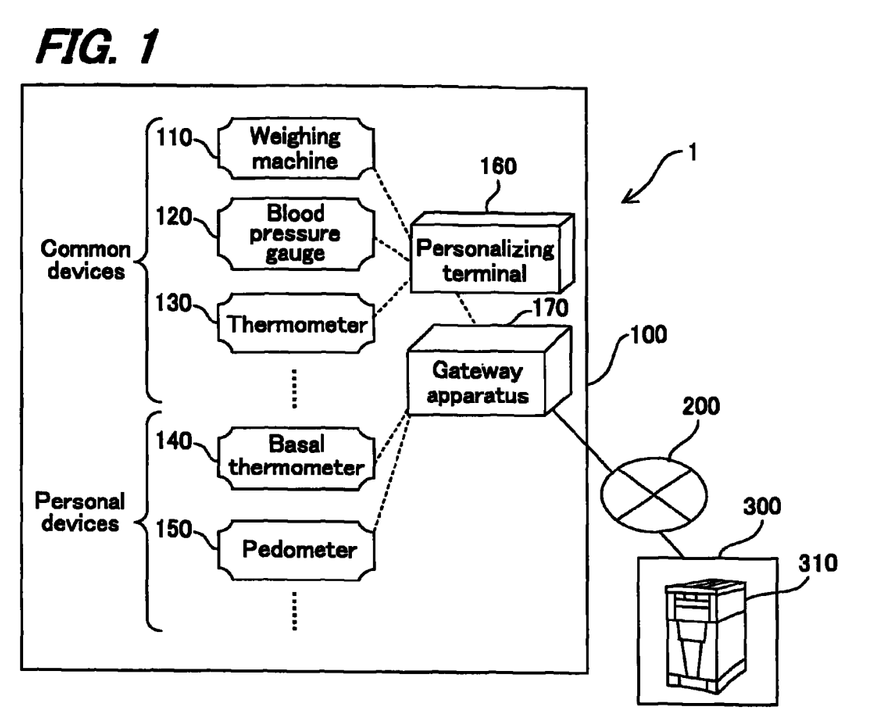
FIG. 1 is a view showing the outline of a health management system according to the present invention.

FIG. 1 is a view showing the outline of a health management system 1 according to the present invention.

In FIG. 1, an in-home system 100 is composed of common health data measuring devices 110, 120 and 130 (which will be referred to hereinbelow as "common devices") that are shared by a plurality of users, personal health data measuring devices 140 and 150 (which will be referred to hereinbelow as "personal devices") dedicated for a particular user, a personalizing terminal 160 for integrating the health data measured or calculated by common devices 110 to 130 and allotting a user ID to the data, and a gateway apparatus 170 for collecting the health data with user IDs from personalizing terminal 160, personal device 140 or 150.

Gateway apparatus 170 is also connected to a data center 300 including a server apparatus 310 for collecting and storing health data by way of a public line 200 such as the internet etc.

Though FIG. 1 is illustrated on the assumption that personal devices 140 and 150 transmit data to gateway apparatus 170, personal devices 140 and 150 may be configured so as to transmit data to personalizing terminal 160.

Figure 2:
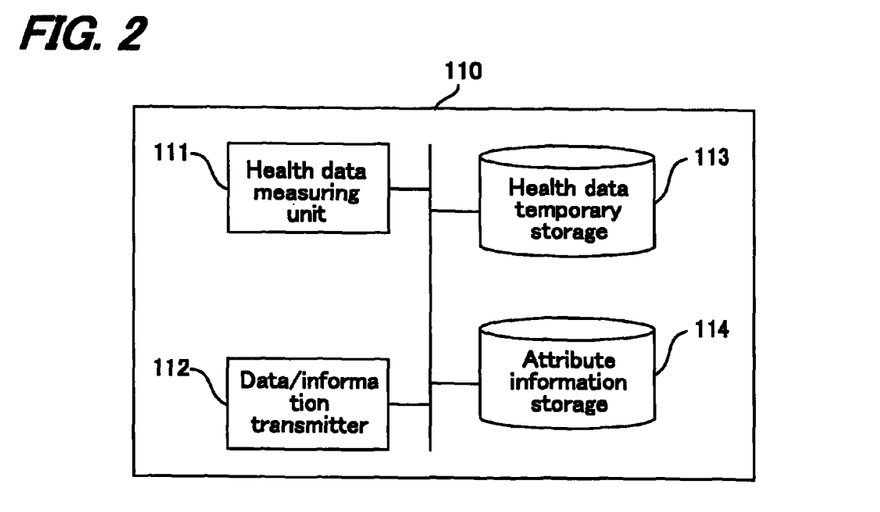
FIG. 2 is a functional block diagram of a common device.

FIG. 2 is a functional block diagram of common devices 110 to 130 shown in FIG. 1.

Common devices 110 to 130 have the same configurations, so that description herein will be made as to common device 110.

Common device 110 is composed of a health data measuring unit 111, a data/information transmitter 112, a health data temporary storage 113 and an attribute information storage 114.

Health data measuring unit 111 temporarily stores measured or calculated health data into health data temporary storage 113.

Stored in attribute information storage 114 is attribute information comprising basic device attribute information on the common device and health data attribute information relating to the health data measured by the common device. Examples of the device attribute information include the device ID of the common device, the maker name, the model number, serial number and the like. The health data attribute information includes, for example, the type of health data, unit or scale, and the like.

Data/information transmitter 112 transmits the health data stored in health data temporary storage 113 and the attribute information stored in attribute information storage 114 to personalizing terminal 160.

It is preferable that the health data is transmitted immediately after when health data measuring unit 111 has finished measurement or calculation. On the other hand, the attribute data may be transmitted simultaneously with transmission of the health data or may be transmitted in advance.

When the attribute information is transmitted simultaneously with the health data, the device attribute information on the common device 110 and the health data attribute information relating to the health data are transmitted together with the health data. On the other hand, when the attribute information is transmitted in advance, it is preferable that the device attribute information on the common device 110 and the health data attribute information relating to all the health data measured or calculated by the common device 110 are transmitted.

Figure 3:
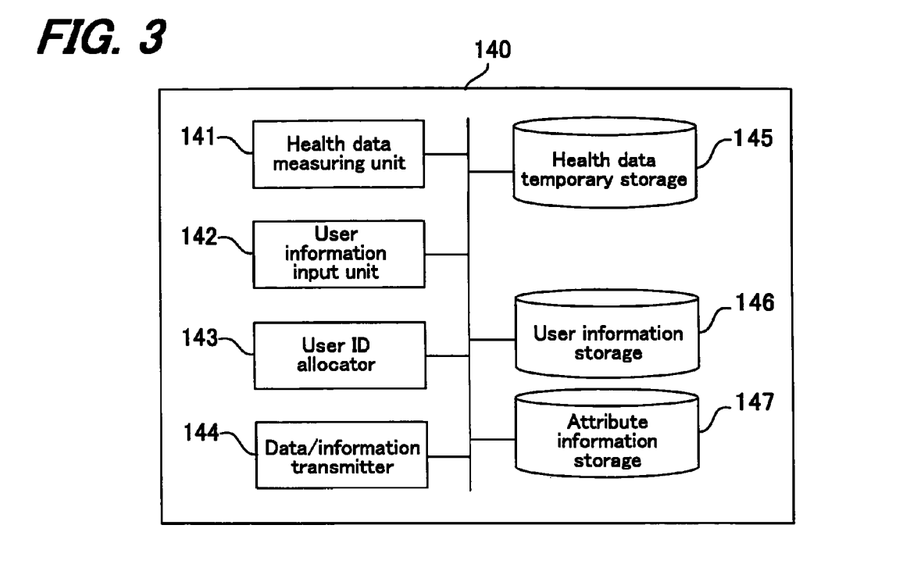
FIG. 3 is a functional block diagram of a personal device.

FIG. 3 is a functional block diagram of personal device 140 or 150 shown in FIG. 1.

Since personal devices 140 and 150 have similar configurations, so that description herein will be made of personal device 140.

Personal device 140 is composed of a health data measuring unit 141, a user information input unit 142, a user ID allocator 143, a data/information transmitter 144, a health data temporary storage 145 as a memory, a user information storage 146 and an attribute information storage 147.

The user of personal device 140 enters user information including an user ID through user information input unit 142 so as to personalize the personal device 140 for the user. The input user information is stored into user information storage 146.

The personal device may be constructed such that information on a plurality of users is enterable and a plurality of user information are registered in user information storage 146 and that the device is temporarily personalized by identifying the user based on the user ID or the like every time the user uses.

Alternatively, since the user information also has been stored in personalizing terminal 160 or gateway apparatus 170, when the user ID or the like is unified between personal devices 140, 150, personalizing terminal 160 and gateway apparatus 170 it is possible for the device to download the user information from personalizing terminal 160 or gateway apparatus 170 and store it into user information storage 146 as the user enters his/her user ID or the like.

The health data measured or calculated by health data measuring unit 141 is given with the user ID stored in user information storage 146 by user ID allocator 143 and temporarily stored in health data temporary storage 145.

Stored in attribute information storage 147 is attribute information consisting of basic device attribute information on the personal device 140 and health data attribute information as to the health data to be measured by the personal device 140. Contents of the personal device attribute information and the health data attribute information are the same as those in attribute information storage 114 in common device 110 of FIG. 2.

Data/information transmitter 144 transmits the health data stored in health data temporary storage 145 and the attribute information stored in attribute information storage 147 to personalizing terminal 160 or gateway apparatus 170 in FIG. 1. It is not specified that the health data and attribute information sent out from data/information transmitter 144 should be transmitted to either personalizing terminal 160 or gateway apparatus 170.

Though it is preferable that the health data is transmitted immediately after when health data measuring unit 141 has finished measurement or calculation, the data may be transmitted at the predetermined time or periodically. On the other hand, the attribute data may be transmitted simultaneously with transmission of the health data or may be transmitted in advance.

When the attribute information is transmitted simultaneously with transmission of the health data, the device attribute information on the personal device 140 and the health data attribute information as to the health data are transmitted together with the health data. On the other hand, when the attribute information is transmitted in advance, it is preferable that the device attribute information on the personal device 140 and the health data attribute information as to all the health data measured or calculated by the personal device 140 are transmitted.

Figure 4:
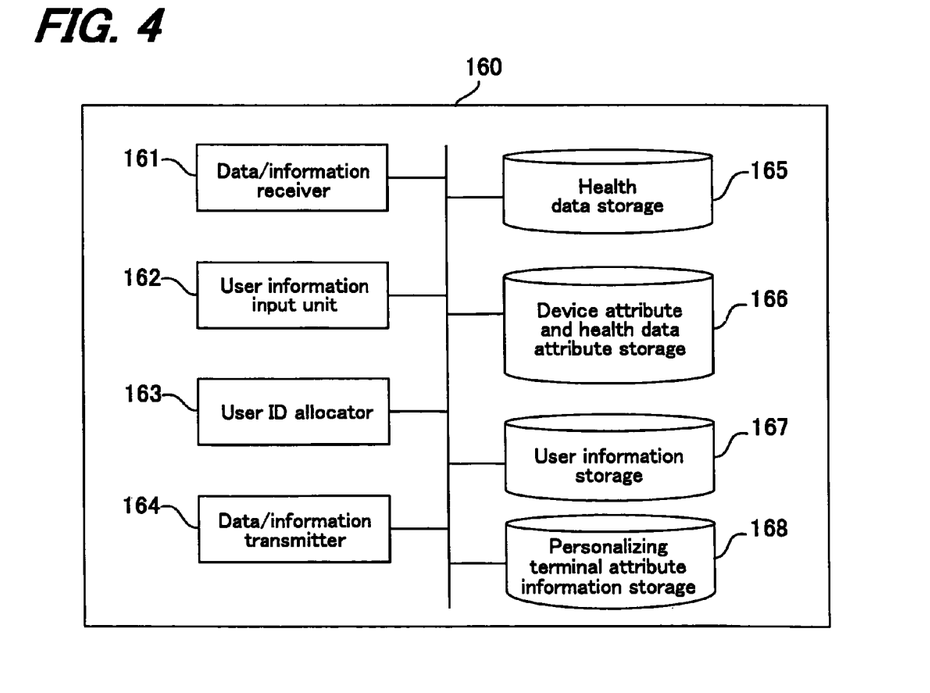
FIG. 4 is a functional block diagram of a personalizing terminal.

FIG. 4 is a functional block diagram of personalizing terminal 160 in FIG. 1.

Personalizing terminal 160 is preferably a handy-to-carry compact terminal such as a compact personal information terminal, cellular phone, and the like.

If personalizing terminal 160 is handy to carry, the user can put personalizing terminal 160 by the side when using common devices 110 to 130 and can enter user's information to personalizing terminal 160 so as to personalize the personalizing terminal 160 for the user, whereby the data that personalizing terminal 160 receives will be regarded as the data on the user who personalizes the terminal, hence will be added with the ID of the user. With this arrangement, personalizing terminal 160 after it has received the health data and attribute information transmitted from common devices 110 to 130, can smoothly perform a user ID allocating process and a forwarding process to gateway apparatus 170 in a cooperative manner, hence operation convenience can be enhanced.

Personalizing device 160 is composed of a data/information receiver 161, a user information input unit 162, a user ID allocator 163, a data/information transmitter 164, a health data storage 165 as a memory, a device attribute and health data attribute storage 166, a user information storage 167 and a personalizing terminal attribute information storage 168.

The user of personalizing device 160 enters user information including a user ID through user information input unit 162 so as to personalize the personalizing device 160 for the user. The input information on the user is stored into user information storage 167.

The device may be constructed such that information on a plurality of users can be entered and a plurality of user information are registered in user information storage 167 and that the device is temporarily personalized by identifying the user based on the user ID or the like input every time the user uses. Alternatively, under the condition that user IDs or the like are unified in advance between personalizing terminal 160 and gateway apparatus 170, user information may be downloaded from gateway apparatus 170 when the user inputs the user ID or the like, or user information may be transmitted or obtained in any other way from another terminal and can be stored into user information storage 167.

Data/information receiver 161 receives health data and attribute information from one or more arbitral terminals among common devices 110 to 130, personal devices 140 and 150 in FIG. 1.

Here, health data with no user ID received from common devices 110 to 130 is allotted with the user ID stored in user information storage 167 by user ID allocator 163. That is, in personalizing terminal 160, health data with no user ID received from common device 110 to 130 is regarded as the data of the user who uses the personalizing terminal 160.

Health data, having user ID or having been allotted with user ID by user ID allocator 163, is stored in health data storage 165 which temporarily or permanently stores the health data while the attribute information on common devices 110 to 130 or personal devices 140 and 150 is stored in device attribute and health data attribute storage 166.

Stored in personalizing terminal attribute information storage 168 is basic attribute information on the personalizing terminal 160. Examples of the attribute information include the device ID, the maker name, the model number, serial number and the like of the personalizing terminal 160.

Data/information transmitter 164 transfers the health data stored in health data storage 165 and the attribute information stored in device attribute and health data attribute storage 166 to gateway apparatus 170 in FIG. 1. As to timing of transferring the attribute information, it may be transmitted simultaneously with transfer of the health data or may be transmitted in advance.

For example, when attribute information is received with health data from an arbitrary one of common devices 110 to 130, personal devices 140 and 150, the attribute information is similarly transferred with the health data without its content changed to gateway apparatus 170.

On the other hand, when attribute information has been received from an arbitrary one of common devices 110 to 130, personal devices 140 and 150, the attribute information is stored in device attribute and health data attribute storage 166, and then the attribute information may be transferred to gateway apparatus 170 from when the attribute information was received until health data is received. Alternatively, after reception of health data, the device attribute of the device transmitted the health data and the health data attribute on the health data may be retrieved from device attribute and health data attribute storage 166 to be transferred with the health data to gateway apparatus 170.

Here, health data stored in health data storage 165 and attribute information stored in device attribute and health data attribute storage 166 may be deleted after completing transmission of the health data and attribute information or may be permanently stored as long as the memory has available space.

Figure 5:
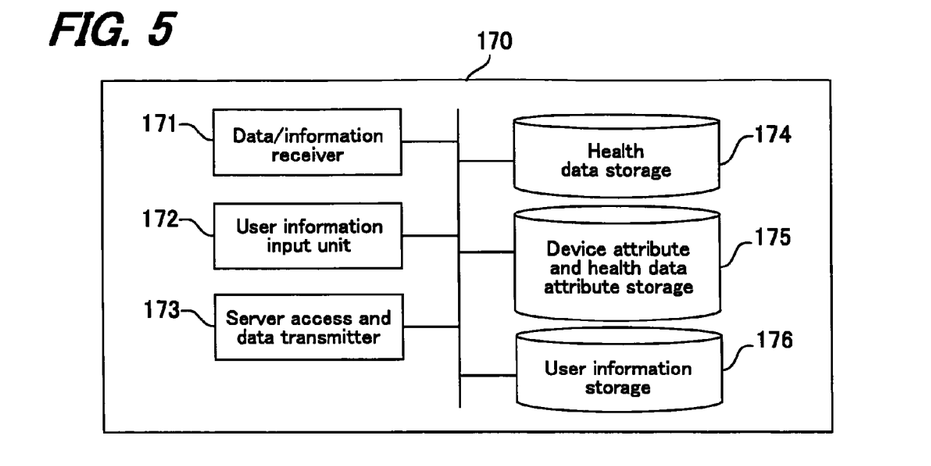
FIG. 5 is a functional block diagram of a gateway apparatus.

FIG. 5 is a functional block diagram of gateway apparatus 170 in FIG. 1.

Gateway apparatus 170 is composed of a data/information receiver 171, a user information input unit 172, a server access and data transmitter 173, a health data storage 174 as a memory, a device attribute and health data attribute storage 175 and a user information storage 176.

User information including the user IDs of all the users in in-home system 100 in FIG. 1 and the management IDs in server apparatus 310 in data center 300 is input via user information input unit 172 and stored into user information storage 176. Input of user information may be done directly into gateway apparatus 170 or may be done by transmission from common device 110 to 130, personal device 140, 150, personalizing terminal 160, any other terminal or server apparatus 310.

Data/information receiver 171 receives health data and attribute information from arbitrary one or more terminals of personalizing terminal 160, personal devices 140 and 150 in FIG. 1. The health data is stored into health data storage 174 while the attribute information on the common devices 110 to 130 or the personal devices 140 and 150 and the attribute information on the health data are stored into device attribute and health data attribute storage 175.

Server access and data transmitter 173 generates access information including log-in information for making access to server apparatus 310 in data center 300 in FIG. 1 and makes access to the server apparatus 310. After logging in server apparatus 310, the transmitter sends out the unsent health data stored in health data storage 174 with the user management ID that has been given by data center 300 and is stored in user information storage 176. It should be noted that the method of transmitting attribute information to server apparatus 310 depends on individual communication scheme with server apparatus 310.

The health data and user management ID sent out from gateway apparatus 170 in FIG. 1 is received by server apparatus 310 in data center 300 and stored therein.

Now, the flow of integrating health data in the present embodiment will be described.

Transmission of health data or attribute information between the sender (data sender) and the receiver (data receiver) is realized such that one (the trigger node) of the two makes a start and the other (the answer node) receiving it answers. In the present embodiment, any one of the following three modes may be used to perform transmission between the sender and the receiver.

(1) When the sender is the trigger node, transmission is carried out in the notice-and-confirmation mode whereby the sender sends out health data or attribute information and the receiver as the answer node returns the validity of reception.

(2) When the receiver is the trigger node, transmission is carried out in the request-and-response mode whereby the receiver makes a request to the sender to send out health data or attribute information and the sender receiving it as the answer node transmits health data or attribute information to the receiver.

(3) As a special mode of the notice-and-confirmation mode, transmission is carried out in a mode whereby only notice is given while the receiver as the answer node will not return any result.

The above processes (1) to (3) are implemented between data/information transmitters 112 and 114 of common device 110 to 130, personal device 140 or 150 and data/information receiver 161 of personalizing terminal 160, or between data/information transmitter 144 of personal device 140, 150, or data/information transmitter 164 of personalizing terminal 160, and data/information receiver 171 of gateway apparatus 170.

When checking the validity of the transmission and reception timing and receiving the notice from the opposite terminal that the opposite terminal cannot establish communication at present, the process is ended there and then. It is preferred that the control is set up so that the opposite terminal will be checked about the transmission and reception timing once again after a lapse of a certain period or after a lapse of a random period.

Next, the flow of integrating health data according to the present embodiment will be described with reference to the drawings.

Figure 6:
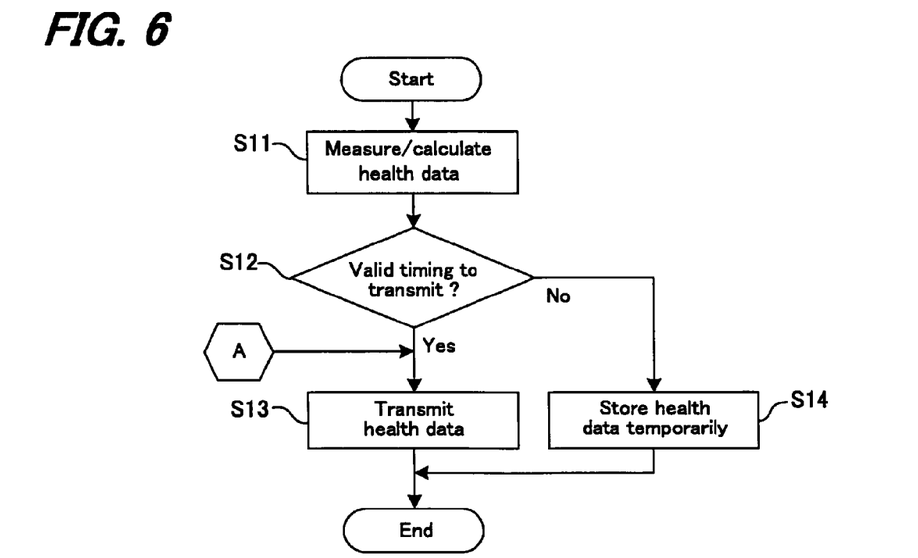
FIG. 6 is a flow chart of transmission of health data to a personalizing terminal from a common device.

FIG. 6 is a flow chart of transmission of health data to personalizing terminal 160 in common devices 110 to 130 in FIG. 1.

At S11, health data measuring unit 111 measures or calculates health data. At S12, data/information transmitter 112 checks personalizing terminal 160 in the manner stated above to determine whether it is the valid timing to transmit the health data, and if it is the valid timing to transmit, the transmitter transmits the health data from health data temporary storage 113, and also retrieves the attribute information from attribute information storage 114 if attribute information needs to be transmitted at the same time, and transmits them together. When it is determined that it is not the valid timing of transmission, from a notice or the like from personalizing terminal 160, data/information transmitter 112 temporarily stores the health data into health data temporary storage 113 at S14.

Here, the health data to be transmitted at S13 is unsent data that has been stored in health data temporary storage 113, and is preferably deleted after transmission in order to protect privacy since common devices 110 to 130 are used by other users and in order to minimize the memory.

When data is transmitted in answer to a request from the personalizing terminal 160 for acquiring heath data in the request-and-response mode, the flow starts from A in FIG. 6.

Figure 7:
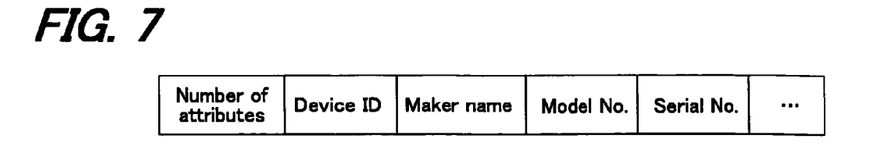
FIG. 7 is a diagram showing the image of device attribute information.
Figure 8:
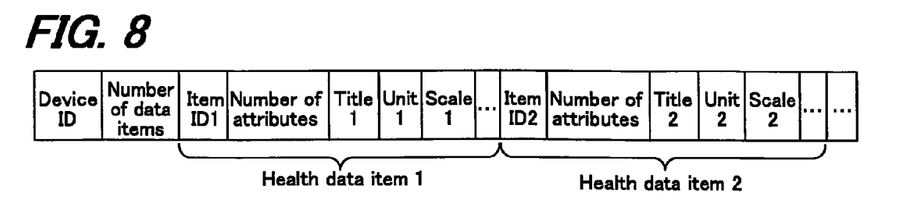
FIG. 8 is a diagram showing the image of health data attribute information.
Figure 9:
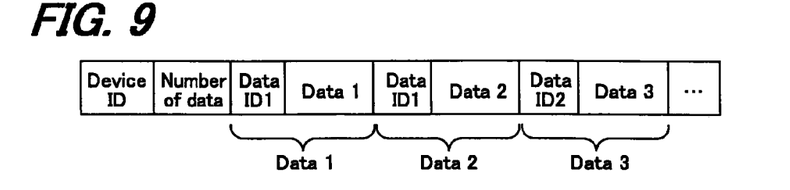
FIG. 9 is a diagram showing the image of health data transmitted from a common device.

The image of the attribute information of a device is shown in FIG. 7, the image of the attribute information of health data is shown in FIG. 8, and the image of the health data transmitted from common devices 110 to 130 is shown in FIG. 9.

As the device attribute information, for example, the number of attributes, device ID, maker name, model number, serial number and the like can be listed as shown in FIG. 7.

As the attribute information of health data, for example, the number of data items, individual health data items and the like may be preferably described in relation with the ID of the device that measures the health data, as shown in FIG. 8. For each health data item, item ID, the number of attributes, title of health data, unit, scale and the like can be listed.

Further, health data is preferably described with the number of data and individual pieces of data in relation with the ID of the device that measured the health data, as shown in FIG. 9. For each data, the data is preferably described in relation with a data ID.

These pieces of data may be transmitted being correlated with each other or may be transmitted individually. When the attribute information on the device and that on health data are transmitted individually, it is preferable to transmit them continuously.

Figure 10:
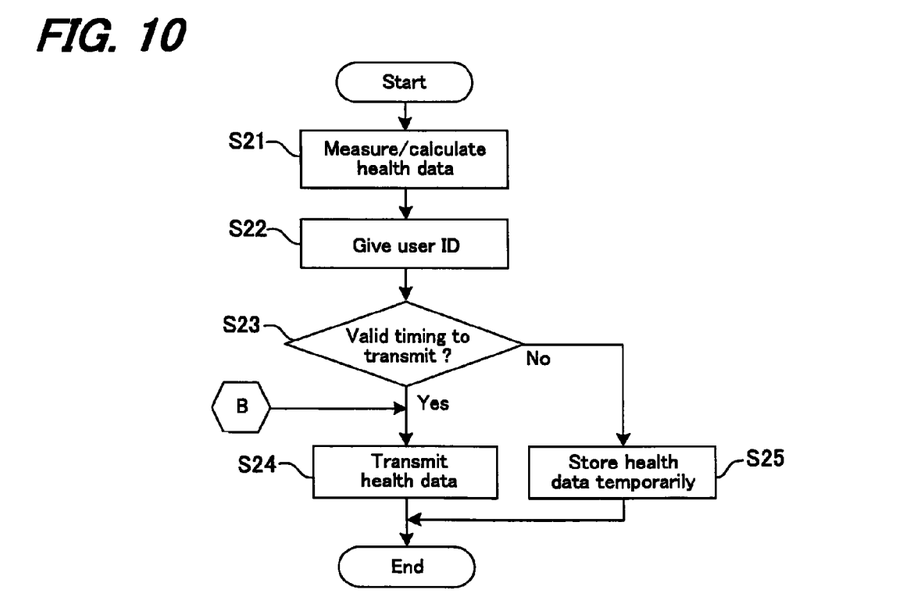
FIG. 10 is a flow chart of transmission of health data to a gateway apparatus or a personalizing terminal from a personal device.

FIG. 10 is a flow chart when personal device 140 or 150 shown in FIG. 1 transmits health data to gateway apparatus 170 or personalizing terminal 160.

Description hereinbelow will be made on the assumption that personal device 140 or 150 has been input with user information and hence personalized.

At S21, health data measuring unit 141 measures or calculates health data, and at S22 user ID allocator 143 allots the health data the user ID stored in user information storage 146.

Next, at S23, data/information transmitter 144 checks gateway apparatus 170 or personalizing terminal 160 in the manner stated above to determine whether it is the valid timing to transmit the health data allotted with the user ID, and if it is the timing to transmit, at S24 the transmitter sends the data to gateway apparatus 170 or personalizing terminal 160. Otherwise, data/information transmitter 144 temporarily stores the health data into health data temporary storage 145 at S25.

Alternatively, instead of transmitting health data etc. to gateway apparatus 170 or personalizing terminal 160 immediately after measurement or calculation of health data, the data may be transmitted at the predetermined time or periodically. In this case, the health data is immediately stored into health data temporary storage 145 immediately after measurement or calculation, and then data/information transmitter 144 transmits the health data etc. to gateway apparatus 170 or personalizing terminal 160 at the predetermined time or periodically.

Here, the health data to be transmitted at S24 is unsent data that has been stored in health data temporary storage 145, and is preferably deleted after transmission in order to protect privacy since personal devices 140 and 150 may be used by other users when a plurality of users can be registered, and in order to minimize the memory.

When an acquisition request for health data was made from gateway apparatus 170 or personalizing terminal 160 in request-and-response mode, the flow starts from B in FIG. 10.

Figure 11:
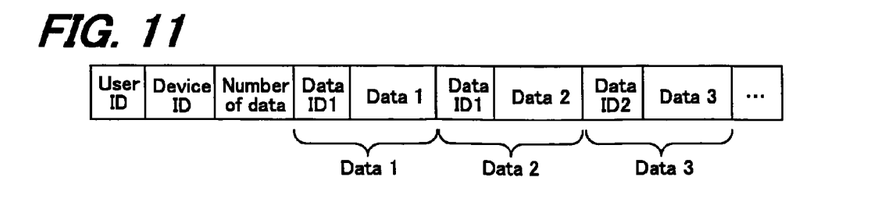
FIG. 11 is a diagram showing the image of health data transmitted from a personal device.

The image of the attribute information of a device is shown in FIG. 7, the image of the attribute information of health data is shown in FIG. 8, and the image of health data transmitted from personal device 140 or 150 is shown in FIG. 11.

The device attribute information and health data attribute information are the same as those described as to common devices.

Health data is preferably described with the number of data and individual pieces of data in relation with the ID of the user measured the health data and the device ID, as shown in FIG. 11. For each data, the data is preferably described in relation with a data ID.

These pieces of data may be transmitted being correlated with each other or may be transmitted individually. When the attribute information on the device and that on health data are transmitted individually, it is preferable to transmit them continuously.

Figure 12:
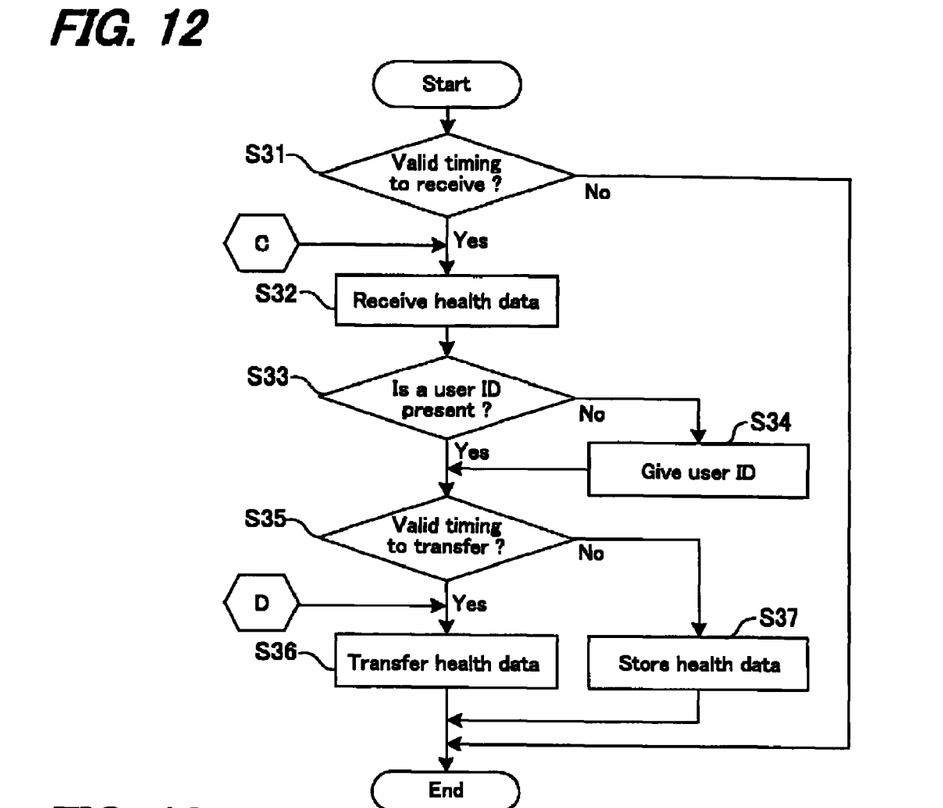
FIG. 12 is a flow chart when a personalizing terminal receives health data from a common device or a personal device and transmits health data to a gateway apparatus.

FIG. 12 is a flow chart when personalizing terminal 160 in FIG. 1 receives health data from common device 110 to 130, personal device 140 or 150 and transmits the health data to gateway apparatus 170.

Description hereinbelow will be made on the assumption that personalizing terminal 160 has been input with user information and hence personalized.

At S31, data/information receiver 161 checks common device 110 to 130, personal device 140 or 150, i.e., the health data measuring device, in the manner stated above to determine whether it is the valid timing to be able to transmit health data, and if it is the right timing for personalizing terminal 160, then the operation goes to S32 to receive health data. Otherwise, the operation is ended.

When a notice was given from the health data measuring apparatus in notice-and-confirmation mode or notice mode, the flow starts from C in FIG. 12.

Next, at S33, user ID allocator 163 determines whether the received health data has been given with a user ID, and if no user ID has been given, the operation goes to S34, where it calls user information from user information storage 167 and gives the user ID included in the user information to the health data. That is, in personalizing terminal 160, health data without any user ID received from common devices 110 to 130 is regarded as the data of the user who uses the personalizing terminal 160.

The image of device attribute information is shown in FIG. 7, the image of health data attribute information is shown in FIG. 8, and the image of health data, allotted with user ID, to be transmitted from personalizing terminal 160 is exemplified in FIG. 11.

The device attribute information, health data attribute information and health data are the same as those described as to common devices and personal devices.

These pieces of data may be transmitted and received being correlated with each other or may be transmitted and received individually. When the attribute information on the device and that on health data are transmitted and received individually, it is preferable to transmit and receive them continuously.

Figure 13:
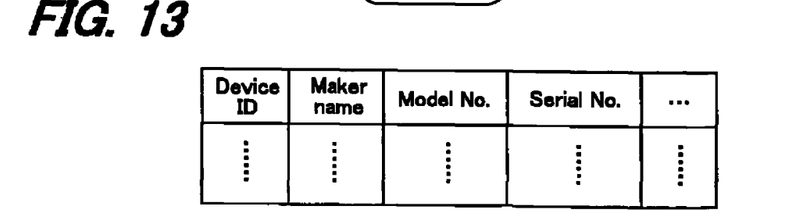
FIG. 13 is a chart showing a table of device attributes.
Figure 14:
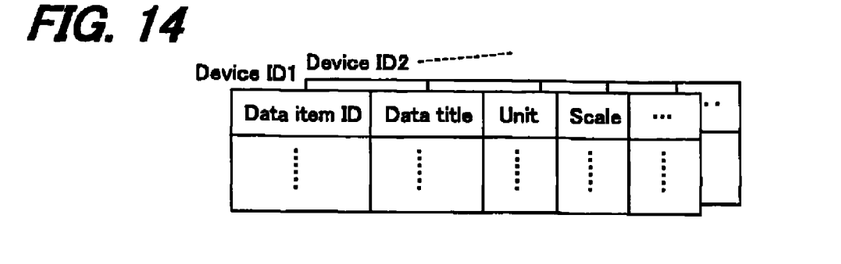
FIG. 14 is a chart showing a table of health data attributes.

Attribute information may be given in table formats shown in FIGS. 13 and 14. Here, FIG. 13 shows an example of table of device attributes and FIG. 14 shows an example of a table of health data attributes.

Next, at S35 data/information transmitter 164 checks gateway apparatus 170 in the manner stated above to determine whether it is the valid timing to transfer the health data allotted with the user ID to gateway apparatus 170, and if it is the timing to transfer, the transmitter sends the data at S36. Otherwise, data/information transmitter 164 temporarily stores the health data into health data temporary storage 165 at S37.

Alternatively, instead of transmitting health data etc. to gateway apparatus 170 immediately after reception of health data etc. or allocation of user ID, the data may be transmitted at the predetermined time or periodically. In this case, the health data etc. is immediately stored into health data storage 165 immediately after reception of health data etc. or allocation of user ID, and then data/information transmitter 164 transmits the health data etc. to gateway apparatus 170 at the predetermined time or periodically.

Here, the health data to be transmitted at S36 is unsent data that has been stored in health data storage 165, and is preferably deleted after transmission in order to protect privacy since personalizing terminal 160 may be used by other users when a plurality of users can be registered, and in order to minimize the memory.

When an acquisition request for health data was made from gateway apparatus 170 in request-and-response mode, the flow starts from D in FIG. 12.

Figure 15:
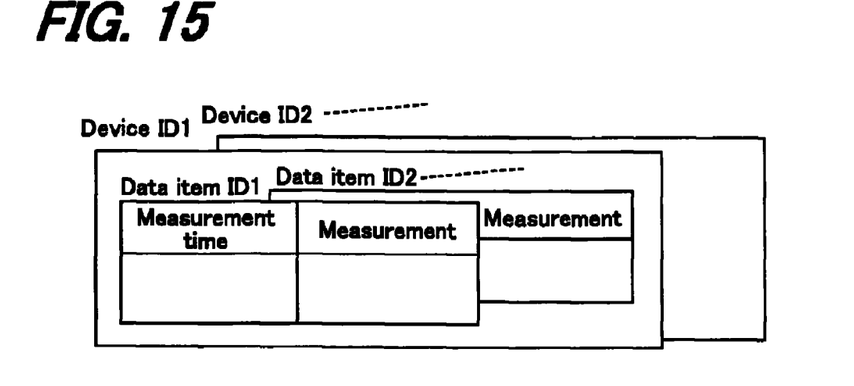
FIG. 15 is a chart showing a table of health data.

The storage format of health data in health data storage 165 may take the form of the image exemplified in FIG. 11 or may be given in a table form exemplified in FIG. 15.

Figure 16:
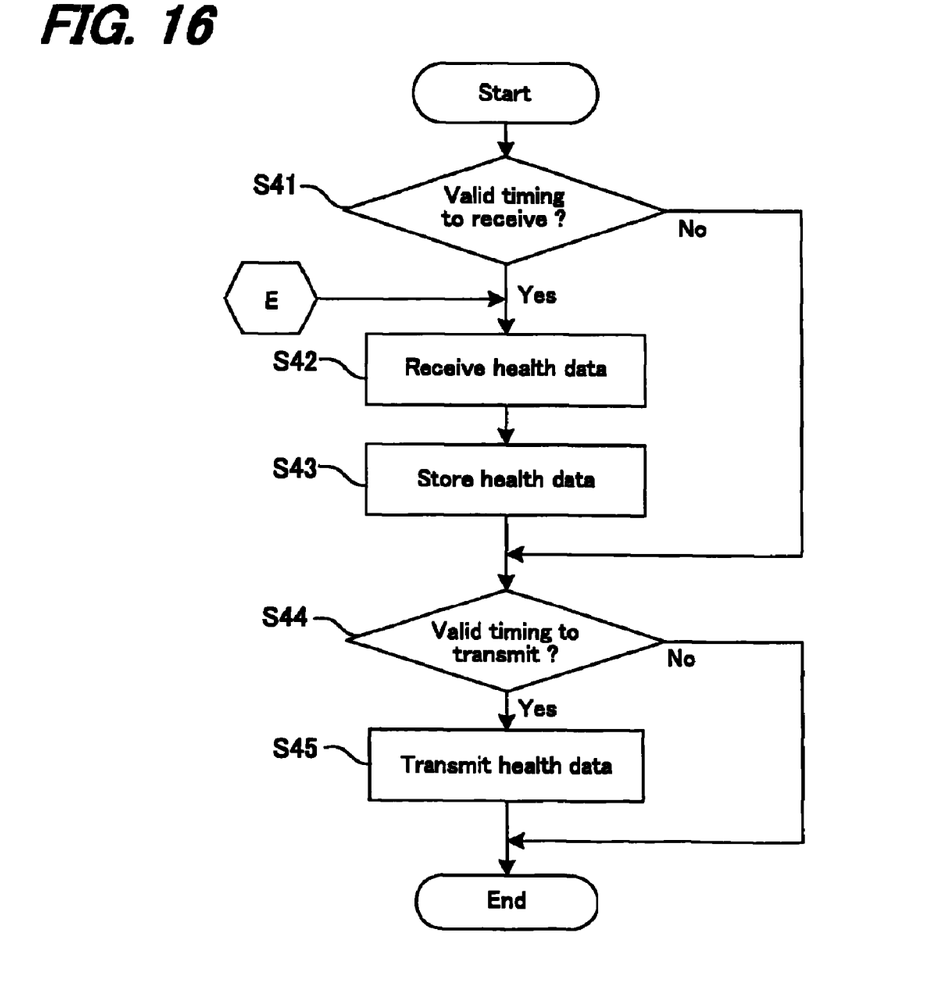
FIG. 16 is a flow chart of transmission and reception of health data in a gateway apparatus.

FIG. 16 is a flow chart showing health data transmission and reception in gateway apparatus 170 in FIG. 1.

At S41, data/information receiver 171 checks personalizing terminal 160, personal device 140 or 150 in the manner stated above to determine whether it is the valid timing to be able to transmit health data, and if it is the right timing to receive health data from personalizing terminal 160, personal device 140 or 150, then the operation goes to S42 to receive health data. Otherwise, the operation is ended.

When a notice was given from personalizing terminal 160, personal device 140 or 150 in notice-and-confirmation mode or in notice mode, the flow starts from E in FIG. 16.

Next, at S43 data/information receiver 171 stores the received health data into health data storage 174. The storage format in health data storage 174 is exemplified in FIG. 15. Health data is stored in a table format in FIG. 15 for each user.

Next, at S44 server access and data transmitter 173 checks server apparatus 310 in data center 300 in FIG. 1 in the manner stated above to determine whether it is the valid timing to be able to receive health data, and if it is the timing to be able to transmit health data to server apparatus 310, the transmitter generates access information (log-in information etc.) to server apparatus 310 to access server apparatus 310 and sends out health data at S45. If server access and data transmitter 173 receives a notice indicating that server apparatus 310 is not ready for reception at present, that is, if it is not a state of being unable to transmit health data, server access and data transmitter 173 ends the operation.

Here, the health data to be sent out at S45 is unsent data that has been stored in health data storage 174.

The timing of transmission at S44 is arbitrary, but transmission is preferably practiced at a predetermined time or at intervals of a predetermined period.

Any access means can be used to access server apparatus 310. For example, protocols on the internet, i.e., http (Hyper Text Transfer Protocol), ftp (File Transfer Protocol) and the like are used. For security assurance, SSL/TLS (Secure Sockets Layer/Transport Layer Security) is preferably used in combination.

Though 100 was assumed to be an in-home system, it may be a system inside a facility. That is, the place of installation of the system is arbitrary and is not limited to the above.

The Second Embodiment

In this embodiment, as to integration of health data of the present invention, a different embodiment from the first embodiment will be described.

The basic flow is the same as that of the first embodiment. In the present embodiment, the devices that transmit and receive health data or attribute information therebetween by way of personalizing terminal 160 are virtualized by personalizing terminal 160. That is, the personalizing terminal 160 looks, to the gateway apparatus 170 side, like a single health data measuring device (personal device) while the personalizing terminal 160 looks, to the health data measuring device side, like a single gateway apparatus 170.

Description below will be made referring to the differences from the first embodiment.

Data/information receiver 161 in personalizing terminal 160 in FIG. 4 corrects individual pieces of health data attribute information, received from a plurality of health data measuring devices and, stored in device attribute and health data attribute storage 166 separately for each health data measuring device so as to be an integrated single piece of health data attribute information.

That is, as shown in FIG. 8, each piece of health data (health data items in the drawing) in the health data attribute information is given with an item ID, but since the item ID is unique to the associated device, data/information receiver 161 of personalizing terminal 160 allots a new item ID to each.

The health data attribute information thus created and unified by data/information receiver 161 is stored in personalizing terminal attribute information storage 168.

Here, it is assumed that device attribute information on the personalizing terminal has been already stored in personalizing terminal attribute information storage 168 as shown in FIG. 7, and data/information receiver 161 also revises the device IDs contained in the health data attribute information to the device ID of personalizing terminal 160 with reference to the device attribute information of the personalizing terminal, as shown in FIG. 8.

Further, data/information receiver 161 also stores a data table of the correspondence relationship between new IDs and old IDs for both device IDs and item IDs.

The data when data/information transmitter 164 transmits attribute information to gateway apparatus 170 is the device attribute information of the personalizing terminal stored in personalizing terminal information storage 168 and the health data attribute information after revision.

Next, the flow of the process by virtualized personalizing terminal 160 will be described.

The following ID converting step is implemented between S32 and S33 in FIG. 12.

Data/information receiver 161, referring to the table of the correspondence relationship between new item IDs and old item IDs stored in personalizing terminal attribute information storage 168, converts the item IDs (data ID in the drawing) of the health data (in FIG. 9 or 11) received from health data measuring devices from old IDs into new IDs. It also converts the device IDs into the device ID of the personalizing terminal 160 by referring to the device attribute information of personalizing terminal 160 stored in personalizing terminal attribute information storage 168.

As described above, modifying the first embodiment as above makes it possible to regard personalizing terminal 160 as a virtual single personal device, hence it is no longer necessary for health data measuring devices (common devices 110 to 130, personal devices 140 and 150) and gateway apparatus 170 to convert individual pieces of attribute information in conformity with other devices, and it is possible to simplify transmission and reception of data between devices of different specifications.

Further, even when the attribute information of each device is modified, if the modified attribute information is transmitted to personalizing terminal 160, the attribute information as the whole system can be updated, hence revision of attribute information can be done simply.

The health management system, personalizing terminal and health management data integrating method according to the present invention should not be limited to the above illustrated examples, but it goes without saying that various changes can be added without departing from the scope of the present invention.

INDUSTRIAL APPLICABILITY

As described heretofore, according to the present invention, in a health management system in which common devices and personal devices coexist, a personalizing terminal receives attribute information and health data from common devices as health data measuring devices, shared by a plurality of persons, adds a user ID to the health data by the user ID allocator and transmits the health data and the attribute information to the gateway apparatus while the gateway apparatus transfers the attribute information and health data having received from the personalizing terminal or personal devices to a server apparatus in a data center, thus making it possible to achieve integration and management by uniting health data with the user who measured the data.

The invention claimed is:

1. A health management system including a health data measuring apparatus for measuring data relating to health of a user, a personalizing terminal for integrating the data and a gateway apparatus, wherein
the health data measuring apparatus includes:
a data measuring unit for measuring or calculating health management data; and
a transmitter for creating first health management data by adding health data measuring apparatus identification information to the health management data, and transmitting the first health management data to the personalizing terminal,
the personalizing terminal includes:
a user information storage having user identification information stored therein;
a user identification information allocator for creating second health management data by adding the user identification information extracted from the user information storage to the first health management data received from the health data measuring apparatus; and,
a transmitter for creating third health management data by converting the health data measuring apparatus identification information included in the second health management data into personalizing terminal identification information of the personalizing terminal, and transmitting the third health management data to the gateway apparatus, and
the gateway apparatus includes:
a data transmitter for transmitting the third health management data received from the health data measuring apparatus to a server apparatus, wherein
a receiver of the personalizing terminal receives device attribute information on the health data measuring apparatus and first data attribute information on the health management data, and creates second data attribute information by converting health data measuring apparatus identification information included in the first data attribute information into the personalizing terminal identification information and stores the second data attribute information into a personalizing terminal attribute information storage and also creates a table that shows a correspondence between the health data measuring apparatus identification information and the personalizing terminal identification information, and stores the table into the personalizing terminal attribute information storage; and,
when receiving the first health management data from the health data measuring apparatus, the receiver of the personalizing terminal converts the health data measuring apparatus identification information included in the first health management data into the personalizing terminal identification information based on the table stored in the personalizing terminal attribute information storage, and,
the transmitter of the personalizing terminal reads out the second data attribute information and the device attribute information from the personalizing terminal attribute information storage and transmits them to the gateway apparatus before or simultaneously with transmission of the third health management data.

2. The health management system according to claim 1, wherein
the measuring unit of the health data measuring apparatus or a receiver of the personalizing terminal stores device attribute information on the health data measuring apparatus and data attribute information on the health management data into an associated device attribute and health data attribute storage, and
the transmitter of the health data measuring apparatus or the transmitter of the personalizing terminal transmits the device attribute information and the data attribute information to the personalizing terminal or the gateway apparatus before, or simultaneously with, transmission of the first health management data or the third health management data.

3. A personalizing terminal for integrating data relating to health of a user, comprising:
a receiver for receiving first health management data including health data measuring apparatus identification information from a health data measuring apparatus;
a user information storage having user identification information stored therein;
a user identification information allocator for creating second health management data by adding the user identification information extracted from the user information storage to the first health management data; and, a transmitter for creating third health management data by converting the health data measuring apparatus identification information included in the second health management data into personalizing terminal identification information of the personalizing terminal, and transmitting the third health management data to a gateway apparatus, wherein the receiver receives device attribute information on the health data measuring apparatus and first data attribute information on the first health management data, and creates second data attribute information by converting health data measuring apparatus identification information included in the first data attribute information into the personalizing terminal identification information and stores the second data attribute information into a personalizing terminal attribute information storage and also creates a table that shows a correspondence between the health data measuring apparatus identification information and the personalizing terminal identification information, and stores the table into the personalizing terminal attribute information storage; and, when receiving the first health management data from the health data measuring apparatus, the receiver converts the health data measuring apparatus identification information included in the first health management data into the personalizing terminal identification information based on the table stored in the personalizing terminal attribute information storage, and the transmitter reads out the second data attribute information and the device attribute information from the personalizing terminal attribute information storage and transmits them to the gateway apparatus before, or simultaneously with, transmission of the third health management data.

4. The personalizing terminal according to claim 3, wherein the receiver stores device attribute information on the health data measuring apparatus and data attribute information on the first health management data received from the health data measuring apparatus, into a device attribute and health data attribute storage; and, the transmitter transmits the device attribute information and the data attribute information to the gateway apparatus before, or simultaneously with, transmission of the third health management data.

5. A health management data integrating method for measuring and integrating data relating to health of users, comprising the steps of:

causing a health data measuring apparatus to execute the steps of:

measuring or calculating health management data; and, creating first health management data by adding health data measuring apparatus identification information to the health management data, and transmitting the first health management data to a personalizing terminal, causing the personalizing terminal to execute the steps of:

creating second health management data by adding user identification information extracted from a user information storage to the first health management data received from the health data measuring apparatus; and, creating third health management data by converting the health data measuring apparatus identification information included in the second health management data into personalizing terminal identification information of the personalizing terminal, and transmitting the third health management data to the gateway apparatus, and causing the gateway apparatus to execute the step of transmitting the third health management data received from the health data measuring apparatus to a server apparatus, causing a measuring unit of the health data measuring apparatus to execute the step of storing device attribute information on the health data measuring apparatus and first data attribute information on the health management data into a device attribute and health data attribute storage, causing a transmitter of the health data measuring apparatus to execute the step of transmitting the device attribute information and the first data attribute information to the personalizing terminal before, or simultaneously with, transmission of the first health management data causing a receiver of the personalizing terminal to execute the steps of:

receiving the device attribute information and the first data attribute information, creating second data attribute information by converting health data measuring apparatus identification information included in the first data attribute information into the personalizing terminal identification information, and storing the second data attribute information into a personalizing terminal attribute information storage;

creating a table that shows a correspondence between the health data measuring apparatus identification information and the personalizing terminal identification information, and storing the table into the personalizing terminal attribute information storage;

when receiving the first health management data from the health data measuring apparatus, converting the health data measuring apparatus identification information included in the first health management data into the personalizing terminal identification information based on the table stored in the personalizing terminal attribute information storage, and causing a transmitter of the personalizing terminal to execute the step of reading out the second data attribute information and the device attribute information from the personalizing terminal attribute information storage and transmitting them to the gateway apparatus before, or simultaneously with, transmission of the third health management data.

6. The health management data integrating method according to claim 5, further comprising the steps of:

causing a receiver of the personalizing terminal to execute the step of storing the device attribute information and the first data attribute information into a device attribute and health data attribute storage; and causing a transmitter of the personalizing terminal to execute the step of transmitting the device attribute information and the first data attribute information to the gateway apparatus before, or simultaneously with, transmission of the third health management data.

* * * * *

UNITED STATES PATENT AND TRADEMARK OFFICE
CERTIFICATE OF CORRECTION

PATENT NO. : 8,140,355 B2
APPLICATION NO. : 12/307610
DATED : March 20, 2012
INVENTOR(S) : Kashiwagi It is certified that error appears in the above-identified patent and that said Letters Patent is hereby corrected as shown below:

Claim 1, (column 16, lines 13-14) change "data received from the health data measuring apparatus to a server apparatus, wherein" to -- data received from the personalizing terminal to a server apparatus, wherein --

Claim 5, (column 18, line 8) change "the health data measuring apparatus to a server" to -- the personalizing terminal to a server --

Signed and Sealed this
Thirty-first Day of July, 2012

David J. Kappos
*Director of the United States Patent and Trademark Office*